(12) United States Patent  
Yamaguchi et al.

(10) Patent No.: US 10,005,799 B2  
(45) Date of Patent: Jun. 26, 2018

(54) BIS (ALKOXYSILYL-VINYLENE) GROUP-CONTAINING SILICON COMPOUND AND PRODUCTION METHOD OF SAME

(71) Applicant: SHIN-ETSU CHEMICAL CO., LTD., Tokyo (JP)

(72) Inventors: Takahiro Yamaguchi, Annaka (JP); Takafumi Sakamoto, Annaka (JP); Taiki Katayama, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days. days.

(21) Appl. No.: 15/683,994

(22) Filed: Aug. 23, 2017

(65) Prior Publication Data

US 2018/0037596 A1 Feb. 8, 2018

Related U.S. Application Data

(62) Division of application No. 15/304,254, filed as application No. PCT/JP2015/052809 on Feb. 2, 2015.

(30) Foreign Application Priority Data

Apr. 25, 2014 (JP) .................................. 2014-091240

(51) Int. Cl.
C07F 7/18 (2006.01)
C07B 61/00 (2006.01)

(52) U.S. Cl.
CPC .............. *C07F 7/1808* (2013.01); *C07F 7/18* (2013.01); *C07F 7/1876* (2013.01); *C07B 61/00* (2013.01)

(58) Field of Classification Search
None
See application file for complete search history.

(56) References Cited

U.S. PATENT DOCUMENTS 5,068,381 A 11/1991 Ito et al.
5,162,478 A 11/1992 Barton
(Continued)

FOREIGN PATENT DOCUMENTS

EP 3 156 458 A1 4/2017
JP 39-27643 B 12/1964
(Continued)

OTHER PUBLICATIONS

Extended European Search Report dated Sep. 27, 2017 in Patent Application No. 15782603.3.
(Continued)

*Primary Examiner* — Robert S Loewe
(74) *Attorney, Agent, or Firm* — Oblon, McClelland, Maier & Neustadt, L.L.P.

(57) ABSTRACT

Provided is an organic silicon compound represented by the following general formula (1)

[Chemical formula 1]

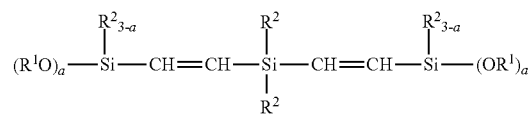

(1)

(wherein $R^1$ represents either an alkyl group that has 1 to 20 carbon atoms and may have a substituted group or a cycloalkyl group that has 3 to 20 carbon atoms and may have a substituted group; $R^2$ represents either a hydrogen atom or a monovalent hydrocarbon group that has 1 to 20 carbon atoms and may have a substituted group, and $R^2$ may be either identical or different; and each a independently represents an integer of 1 to 3).

(Continued)

The novel silicon-containing compound of the present invention provides a cured product of a room temperature-curable organopolysiloxane composition that is particularly superior in fast curability.

1 Claim, 1 Drawing Sheet

(56) References Cited

U.S. PATENT DOCUMENTS

2011/0257324 A1   10/2011   Ziche et al.
2017/0130031 A1   5/2017    Yamaguchi et al.

FOREIGN PATENT DOCUMENTS

| JP | 55-43119 A    | 3/1980  |
| JP | 7-39547 B2    | 5/1995  |
| JP | 7-331076 A    | 12/1995 |
| JP | 2012-511607 A | 5/2012  |

OTHER PUBLICATIONS

N. O. Yarosh, et al., "Synthesis of silanes and germanes with polyunsaturated aliphatic substituents", Russian Chemical Bulletin, vol. 61, No. 10, XP35321387, 2012, pp. 2004-2006.
Yang Luqing, et al., "Charge doping effect on σ-π conjugated copolymers", Science China Chemistry, vol. 54, No. 6, XP19909981, 2011, pp. 975-984.
Yan Shang, et al., "Theoretical studies on organosilicon oligomers containing ethenylene moieties", Journal of Polymer Research, vol. 18, No. 6, XP019981828, 2011, pp. 1889-1902.
L.V. Zhilitskaya, et al., "New Polyunsaturated Silahydrocarbons", Russian Journal of General Chemistry, vol. 79, No. 3, XP55404357, 2009, pp. 383-385.
L.V. Zhilitskaya, et al., "Binuclear Polyunsaturated Organosilicon Dendrimers", Russian Journal of General Chemistry, vol. 77, No. 11, XP55404354, 2007, pp. 1887-1890.
L.V. Zhilitskaya, et al., "Mononuclear Polyunsaturated Organosilicon Dendrimers Simultaneously Containing (CH=CH) and (C=C) Fragments", Russian Journal of General Chemistry, vol. 77, No. 10, XP55404350, 2007, pp. 1718-1723.
Rajsapan Jain, et al., "Bi- and Triferrocene Complexes Containing Silylenevinylenephenylene Bridges. Model Compounds for Poly{ferrocene(phenylene)bis(silylenevinylene)}s", Organometallics, vol. 24, No. 7,XP55404356, 2005, pp. 1468-1476.
Bogdan Marciniec, et al., "Synthesis and structural characterization of trans-tactic vinylene-silylene(siloxylene) polymers", Journal of Physical Organic Chemistry, vol. 16, No. 10, XP55404348, 2003, pp. 818-823.
O.G. Yarosh, et al., "New 15- and 18-Membered Polyunsaturated Macrocyclic Silicohydrocarbons", Russian Journal of General Chemistry, vol. 71, No. 12, XP55404347, 2001, pp. 1869-1873.
N. I. Baklanova, et al., "Thermal Transformations of unsaturated poly(silicohydrocarbons)", Polymer Science, vol. 43, No. 4, XP1063669, 2001, pp. 463-471.
Tadashi Kawai, et al., "Synthesis of σ-π conjugated oligo(silylenevinylene)s by metathesis of divinylsilanes over $Re_2O_7$- $Al_2O_3$ catalyst", Journal of Molecular Catalysis A: Chemical, vol. 160, No. 1, XP55404500, 2000, pp. 173-179.
M.G. Voronkov, et al., "New Polyunsaturated Macrocyclic Silahydrocarbons", Russian Journal of General Chemistry, vol. 70, No. 10, XP9195413, 2000, pp. 1552-1554.
Tadashi Kawai, et al., "Acyclic diene metathesis (ADMET) of vinylsilanes over $Re_2O_7$-$Al_2O_3$ catalyst", Journal of Molecular Catalysis A:Chemical, vol. 140, No. 3, XP55404524, 1999, pp. 287-292.
N. I. Baklanova, et al., "High-Temperature Evolution of SiC/C Products Derived from Preceramic Polymers", Journal of Materials Synthesis and Processing, vol. 7, No. 5, XP55404503, 1999, pp. 289-296.
L.V. Zhilitskaya, et al., "Polyunsaturated Macrocyclic Silahydrocarbons with Exocyclic Trimethylsilylethynyl and N-Trimethylsilylvinyl Groups", Russian Journal of General Chemistry, vol. 69, No. 9, XP9195412, 1999, pp. 1401-1402.
Yukio Kawanami, et al., "Rh(I)-Catalyzed Dehydrogenative Silylation of Divinylsilanes with Dimethylphenylsilane", Bulletin of the Chemical Society of Japan, vol. 69, No. 4, XP55404336, 1996, pp. 1117-1124.
M.G. Voronkov, et al., "Cyclodimethylsilethenes ($Me_2SiCH=CH)_n$," Russian Journal of General Chemistry, vol. 64, No. 3, XP9195411, 1994, pp. 395-396.
V.G. Lakhtin, et al., "Synthesis of 1-trimethylsilyl-2-(Methylchlorosilyl) Ethylenes. I. Reactions of β-Chlorovinyltrimethylsilane with Chlorosilanes in the presence of Sodium", Journal of General Chemistry of the USSR, vol. 62, No. 1, XP9195430, 1992, pp. 84-90 with English translation.
M.G. Voronkov, et al., "Dimethylethynylsilane—a synthon leading to highly unsaturated silicohydrocarbons", Organometallic Chemistry in the USSR, vol. 2, No. 2, XP9195429, 1989, pp. 466-469 with English translation.
O.G. Yarosh, et al., "Organo (β-trifluorosilylviny)silanes", Organometallic Chemistry in the USSR, vol. 1, No. 4, XP9195428, 1988, pp. 430-431.
T.P. Doxopulo, et al., "The Synthesis and Study of some Silicon-Germanium Ethylenic Oligomers", Bulletin of the Academy of Sciences of the Georgian SSR, vol. 116, No. 3, XP9195424, 1984, pp. 529-532 with English summary.
L. P. Asatiani, et al., "Synthesis of Dienic Silicon Derivatives of Ferrocene and Cymantrene", Bulletin of the Academy of Sciences of the Georgian SSR, vol. 90, No. 3, XP9195414, pp. 589-592 with English summary.
O.G. Yarosh, et al., "New Transformations of 1-(Ethynyldimethylsilyl)-2-(trimethylsilyl)-Ethylene", Journal of General Chemistry of the USSR, vol. 48, No. 9, XP9195407, 1978, pp. 1874-1875.
Von G. Fritz, et al., "Bildung siliciumorganischer Verbindungen. LVI[1]) Reaktionen Si—und C-chlorierter 1,3,5-Trisilapentane mit $CH_3MgCI$" Zeitschrift FUR Anorganische UND allgemeine Chemie, vol. 404, No. 2, XP55404323, 1974, pp. 103-120.
I.M. Gverdtsiteli, et al., "Synthesis and Study of Some Unsaturated Silanes on the Base of 1, 4-BIS-(Dimethylsilyl)-1,4-Dihydronaphthalene", Bulletin of the Academy of Science of the Georgian SSR, vol. 65, No. 2, XP9195423, 1972, pp. 349-352 with English summary.
Charles S. Kraihanzel, et al., "Ethynylsilanes II. Syntheses and Characterization of Some Group IV Dimetalloid Acetylenes and Olefins", Journal of Organometallic Chemistry, vol. 10, No. 3, XP55404325, 1967, pp. 427-437.
V. P. Kuznetsova, et al., "Synthesis and Investigation of functional organosilicon compounds containing hydrocarbon bridges between silicon atoms", Journal of General Chemistry USSR, vol. 35, No. 9, XP9195409, 1965, pp. 1636 -1640.
International Search Report dated Apr. 7, 2015 in PCT/JP2015/052809 filed Feb. 2, 2015.
Voronkov, M. G. et al., "Reaction of bis [β-(methyldimethoxysilyl)vinyl] dimethylsilanes and bis [β-(methyldimethoxysilyl)vinyl] methylmethoxysilanes with methylmagnesium iodide", Zhurnal Obshchei Khimii, 1977, vol. 47, No. 4, (2 Pages).
Voronkov, M. G. et al., "Derivatives of methyl substituted trans-1,2-disilylethylene", Izvestiya Akademii Nauk SSSR, Seriya Khimicheskaya, 1974, No. 9, (6 Pages).
Office Action dated May 23, 2017 in Japanese Patent Application No, 2016- 514742 (with English Translation).
Shostakovski et al. "Hydrosilylation of Ethynylsilanes" Irkutsk Institute of Organic Chemistry, Siberian Branch of the Academy of Sciences of the USSR, 7, 1971, 1478-1481.

(56) References Cited

OTHER PUBLICATIONS

Voronkov et al. "Methyl-Substituted trans-1,2-Disilylethylene Derivatives" Irkutsk Institute of Organic Chemistry, Siberian Branch of the Academy of Sciences of the USSR, 9, 1974, 2066-2070.
Office Action dated Apr. 24, 2018 issued in corresponding Chinese patent application No. 201580021814.6 (with English translation).

BIS (ALKOXYSILYL-VINYLENE) GROUP-CONTAINING SILICON COMPOUND AND PRODUCTION METHOD OF SAME

CROSS REFERENCE TO RELATED APPLICATIONS

This application is a divisional application of U.S. patent application Ser. No. 15/304,254, filed on Oct. 14, 2016, which was a 371 application of International Patent Application No. PCT/JP2015/052809, filed on Feb. 2, 2015, and claims priority to Japanese Patent Application No. 2014-091240, filed on Apr. 25, 2014.

TECHNICAL FIELD

The present invention relates to a novel organic silicon compound, especially a novel organic silicon compound useful as a curing agent with an effect of imparting a superior fast curability to a room temperature-curable organopolysiloxane composition; and a production method thereof. In each molecule of such organic silicon compound, provided on an identical silicon atom are two sets of: a hydrolyzable silyl group such as an alkoxysilyl group; and a structure where two silicon atoms are bonded to each other through a carbon—carbon double bond (i.e. silyl-vinylene structure or silyl-ethenylene structure).

BACKGROUND ART

Conventionally, there have been known various types of room temperature-curable compositions capable of being cured into elastomer-like products at room temperature by coming into contact with the moisture in the air. Particularly, those releasing alcohols as they cure are characterized in that they do not produce unpleasant odors and corrode metals, which is why such a type of room temperature-curable compositions have been preferably used in performing sealing, bonding and coating in, for example, electric and electronic equipments.

Typical examples of the above type of room temperature-curable composition include a composition composed of a hydroxyl group-terminated polyorganosiloxane, alkoxysilane and an organic titanium compound; a composition composed of an alkoxysilyl group-terminated polyorganosiloxane, alkoxysilane and alkoxy titanium; a composition composed of a linear polyorganosiloxane containing a silethylene group(s) and terminated by alkoxysilyl groups, alkoxysilane and alkoxy titanium; and a composition composed of a hydroxyl group-terminated polyorganosiloxane or an alkoxy group-terminated polyorganosiloxane and an alkoxy-α-silylester compound (Patent documents 1 to 4).

Although these compositions exhibit a storage stability, a water resistance and a moisture resistance to a certain degree, these properties are not yet completely satisfactory. Further, these compositions have so far exhibited an insufficient fast curability.

As described above, polymers having reactive alkoxysilyl groups on their terminal ends are known. Since these polymers have their polymer terminal ends blocked by alkoxysilyl groups from the beginning, the curability of a composition containing the same is less likely to change (deteriorate) with time, and a superior storage stability can thus be achieved. Further, a workability (viscosity, thixotropy) of such composition can be arbitrarily controlled, and superior properties (hardness, tensile strength and elongation at break) can also be achieved as those polymers form elastomers through reactions with the moisture in the air and then through cross-liking reactions.

However, those of dealcoholization type have exhibited an insufficient curability, since they are less reactive with the moisture in the air as compared to those of other known curing types such as deoximation type, de-acetic acid type and deacetone type.

Here, while developments have been made on a room temperature-curable polyorganosiloxane composition superior in fast curability and capable of forming a cured product superior in moisture resistance, those that can be industrially advantageously produced have not yet been found.

PRIOR ART DOCUMENT

Patent Document

Patent document 1: Japanese Examined Patent Publication No. Sho 39-27643

Patent document 2: JP-A-Sho 55-43119

Patent document 3: Japanese Examined Patent Publication No. Hei 7-39547

Patent document 4: JP-A-Hei 7-331076

Patent document 5: Japanese Unexamined Patent Application Publication (Translation of PCT Application) No. 2012-511607

SUMMARY OF THE INVENTION

Problem to be Solved by the Invention

The present invention was made in view of the above issues, and it is an object of the present invention to provide a curing agent for a room temperature-curable organopolysiloxane composition. The curing agent is especially capable of imparting a fast curability to the room temperature-curable organopolysiloxane composition, and can thus provide a cured product superior in storage stability and durability. Further, the room temperature-curable organopolysiloxane composition can be industrially advantageously produced using a highly general material(s).

Means to Solve the Problem

The inventors of the present invention diligently conducted a series of studies and completed the invention as follows. That is, the inventors found that the hydrolyzability of an alkoxy group in an alkoxysilyl group could be dramatically improved, only when a linking group adjacent to such alkoxysilyl group was a vinylene group (ethenylene group). Specifically, the inventors found that by using a compound that is represented by the following formula (1) and contains alkoxysilyl-vinylene groups, there could be obtained a room temperature-curable composition especially superior in fast curability and capable of forming a cured product with a favorable storage stability and durability. More specifically, the inventors were able to arrive at a room temperature-curable organopolysiloxane composition that can be industrially advantageously produced due to the fact that a highly general material(s) (e.g. diorgano dichlorosilane) can be used as a part of a starting material(s) for producing the above alkoxysilyl-vinylene group-containing compound.

<1>
That is, the present invention is to provide an organic silicon compound represented by the following general formula (1)

[Chemical formula 1]

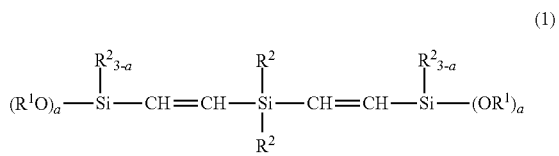

(1)

(wherein $R^1$ represents either an alkyl group that has 1 to 20 carbon atoms and may have a substituted group or a cycloalkyl group that has 3 to 20 carbon atoms and may have a substituted group; $R^2$ represents either a hydrogen atom or a monovalent hydrocarbon group that has 1 to 20 carbon atoms and may have a substituted group, and $R^2$ may be either identical or different; and each a independently represents an integer of 1 to 3). Here, in the present invention, ethenylene group represented by —CH═CH— may be referred to as vinylene group or the like hereunder.
<2>
Further, the present invention provides a production method of the organic silicon compound as set forth in <1>, comprising adding two hydrogenalkoxysilanes (3) to one silane compound (2) having two ethynyl groups on an identical silicon atom, through a hydrosilylation addition reaction

[Chemical formula 2]

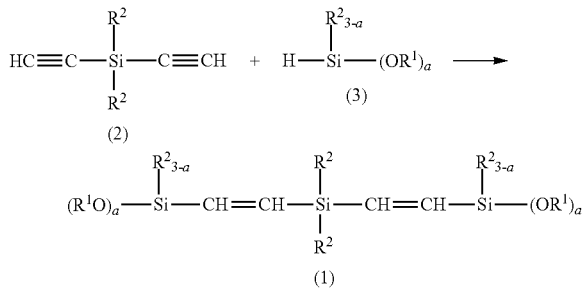

(wherein $R^1$ represents either an alkyl group that has 1 to 20 carbon atoms and may have a substituted group or a cycloalkyl group that has 3 to 20 carbon atoms and may have a substituted group; $R^2$ represents either a hydrogen atom or a monovalent hydrocarbon group that has 1 to 20 carbon atoms and may have a substituted group, and $R^2$ may be either identical or different; and each a independently represents an integer of 1 to 3).

Effects of the Invention

The novel silicon-containing compound of the present invention provides a cured product superior in fast curability, and allows a composition using the same to be quickly cured when exposed to the air even after the composition had been stored for 12 months. Here, a cured product thus obtained exhibits superior properties. Therefore, a composition having, as a curing agent, the novel silicon-containing compound of the present invention (e.g. room temperature-curable organopolysiloxane composition) is useful as a sealing agent, coating material or adhesive agent for use in certain locations where heat resistance, water resistance and moisture resistance are required. Particularly, such composition can be effectively used for construction purposes and applied to an adhesive agent for electric and electronic parts, where steam resistance and water resistance are required. Further, since the silicon-containing compound of the present invention uses a general-purpose chlorosilane, it can be easily industrialized.

MODE FOR CARRYING OUT THE INVENTION

Figure 1:
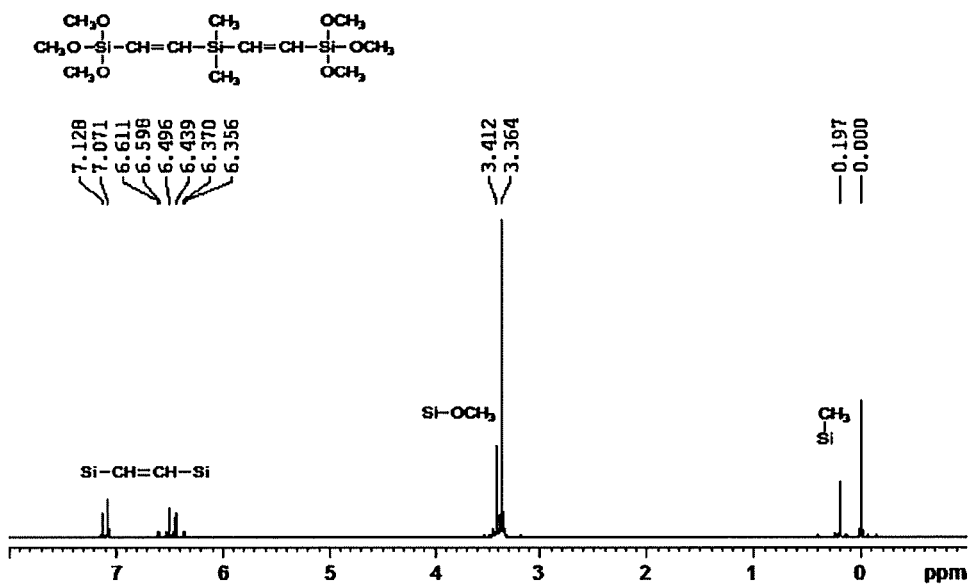
FIG. 1 is a diagram showing a $^1$H-NMR spectrum of a reaction product ([bis (trimethoxysilyl-vinylene) dimethyl-silane]) in a synthesis example 1.
Figure 2:
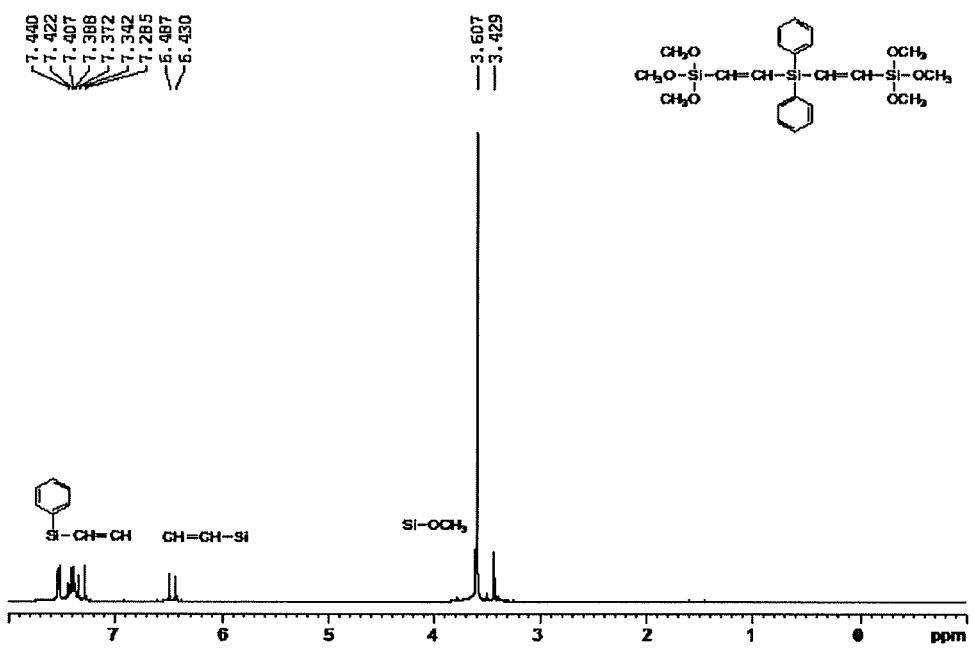
FIG. 2 is a diagram showing a $^1$H-NMR spectrum of a reaction product ([bis (trimethoxysilyl-vinylene) diphenyl-silane]) in a synthesis example 2.

The present invention is described in greater detail hereunder.

<Silicon-containing Compound Terminated by alkoxysilyl-vinylene Group>

The silicon-containing compound terminated by alkoxysilyl-vinylene group which is represented by the above general formula (1) is that having not less than two alkoxysilyl-vinylene bonds on an identical silicon atom (i.e. bis (alkoxysilyl-vinylene) silane compound).

Here, in the above general formula (1), examples of $R^1$ as an alkyl group having 1 to 20 carbon atoms include a methyl group, an ethyl group, an n-propyl group, an isopropyl group, an n-butyl group, an isobutyl group, a tert-butyl group, a pentyl group, a neopentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group and an eicosyl group. Examples of a cycloalkyl group include a cyclopentyl group and a cyclohexyl group. Examples of an alkyl group that has 1 to 20 carbon atoms and may have a substituted group(s), include an aralkyl group such as a benzyl group, a 2-phenylethyl group and a 3-phenylpropyl group. Further, all or a part of the hydrogen atoms in any of these (substituted) alkyl groups may be substituted by, for example, cyano groups and/or halogen atoms such as F, Cl and Br. Examples of a substituted group thus obtained include a 3-chloropropyl group, a 3,3,3-trifluoropropyl group and a 2-cyanoethyl group. Among all the above examples, preferred as $R^1$ are alkyl groups having 1 to 6, particularly 1 to 4 carbon atoms. A methyl group and an ethyl group are more preferred as $R^1$, where a methyl group is even more preferred in terms of availability, productivity and cost.

$R^2$ represents a substituted or unsubstituted monovalent hydrocarbon group having 1 to 20 carbon atoms. $R^2$s may be identical to or different from one another. Examples of such $R^2$ include an alkyl group such as a methyl group, an ethyl group, an n-propyl group, an isopropyl group, an n-butyl group, an isobutyl group, a tert-butyl group, a pentyl group, a neopentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, an octadecyl group, a nonadecyl group and an eicosyl group; a cycloalkyl group such as a cyclopentyl group and a cyclohexyl group; an alkenyl group such as a vinyl group, an allyl group, a butenyl group, a pentenyl group and a hexenyl group; an aryl group such as a phenyl group, a tolyl group, a xylyl group and an α-, β-naphthyl group; and an aralkyl group such as a benzyl group, a 2-phenylethyl group and a 3-phenylpropyl group. $R^2$ may also be a group obtained by substituting a part of or all the hydrogen atoms in any of these groups with, for example, cyano groups and/or halogen atoms such as F, Cl and Br. Examples of such substituted group include a 3-chloropropyl group, 3,3,3-trifluoropropyl group and a 2-cyanoethyl group. Among all the above examples, preferred are monovalent hydrocarbon groups having 1 to 10, particularly 1 to 6 carbon atoms. A methyl group, an ethyl group and a phenyl group are more preferred, where a methyl group and a phenyl group are even more preferred in terms of availability, productivity and cost. Each a independently represents an integer of 1 to 3. However, it is preferred that a be either 2 or 3, more preferably 3.

The organic silicon compound represented by the general formula (1) of the present invention is mainly used as a curing agent for a (room temperature) curable composition. Particularly, those having three methoxy groups on an identical silicon atom in a molecule (six in total per molecule) contain a trifunctional alkoxysilane site(s), and are thus useful as curing agents (cross-linking agent) for a dealcoholized silicone RTV (room temperature-curable organopolysiloxane composition).

<Production Method of Organic Silicon Compound Represented by General Formula (1)>

The silicon-containing compound of the invention which has two alkoxysilyl-vinylene bonds on an identical silicon atom can, for example, be easily produced through an addition reaction such as a hydrosilylation reaction between a silane having two ethynyl groups on an identical silicon atom and two alkoxysilanes (hydrogenalkoxysilane). This reaction is expressed by the following formula [1].

[Chemical formula 3]

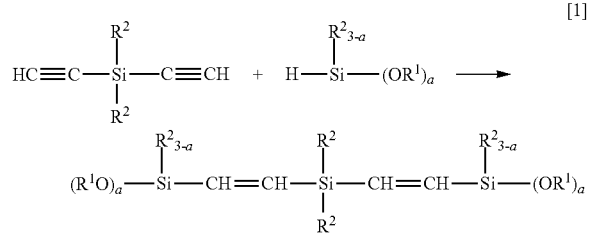

(In the above formula, $R^1$, $R^2$ and a are defined as above.)

As an addition reaction catalyst used when adding alkoxysilane (hydrogenalkoxysilane), platinum group metal-based catalysts such as a platinum-based catalyst, a palladium-based catalyst, a rhodium-based catalyst and a ruthenium-based catalyst are available. Here, a platinum-based catalyst is particularly preferred. Examples of such platinum-based catalyst include a platinum black; a catalyst with a solid platinum being supported on a support such as alumina and silica; a chloroplatinic acid; an alcohol-modified chloroplatinic acid; a complex of a chloroplatinic acid and olefin; and a complex of platinum and vinylsiloxane. These kinds of platinum may be used in a so-called catalytic amount, and may, for example, be used in an amount of 0.1 to 1,000 ppm, particularly 0.5 to 100 ppm in terms of platinum group metal, with respect to alkoxysilanes.

It is desired that this reaction be performed at a temperature of 50 to 120° C., particularly 60 to 100° C., for 0.5 to 12 hours, particularly 1 to 6 hours, and the reaction can be performed without a solvent. However, an appropriate solvent such as toluene and xylene may be used, provided that no adverse impact will be inflicted upon the above addition reaction or the like.

In an addition reaction to silyl-acetylene group (silylethynyl group), a geometric isomer represented by the following reaction formula [2] will, for example, be produced. In such geometric isomer, the production of E isomer (trans isomer) is highly selective and highly reactive. Since there will be no adverse impact on the properties of the silicon-containing compound of the present invention, these geometric isomers need not be separated at the time of use.

[Chemical formula 4]

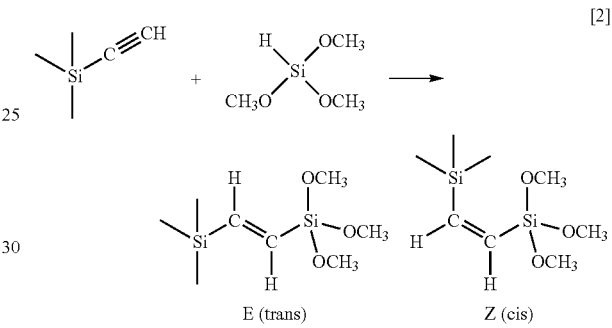

Specific examples of the organic silicon compound represented by the general formula (1) of the invention include those represented by the following structural formulae.

[Chemical formula 5]

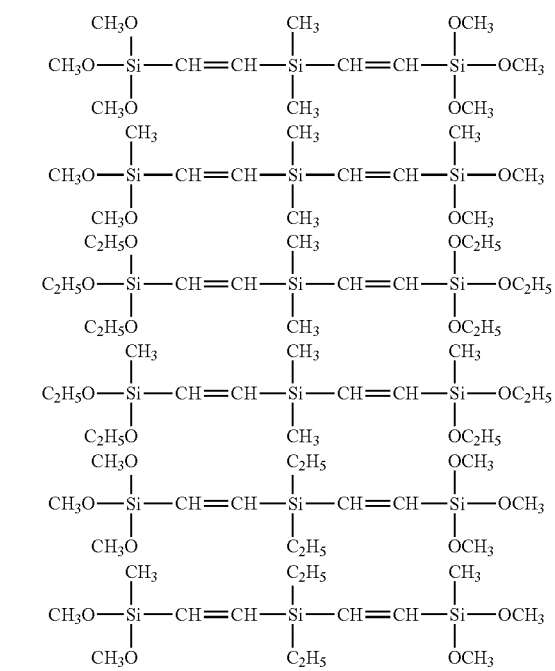

-continued

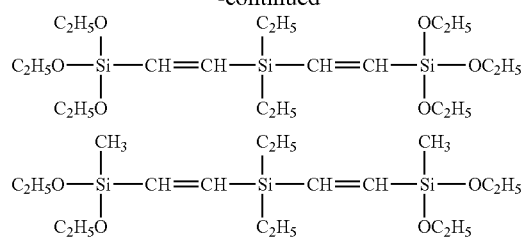

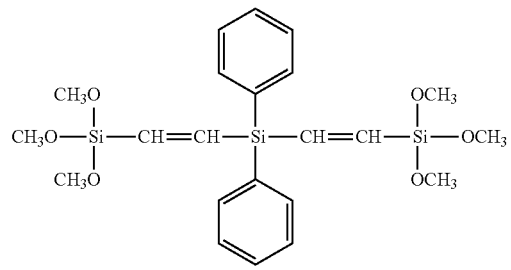

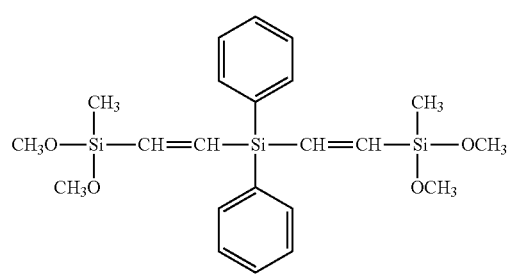

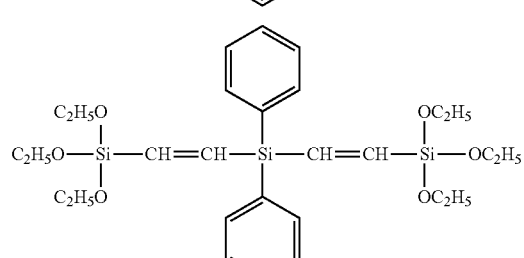

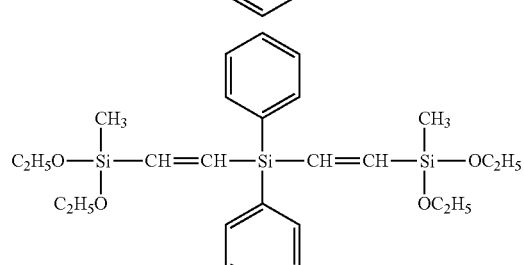

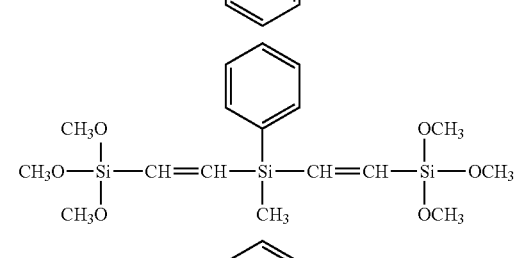

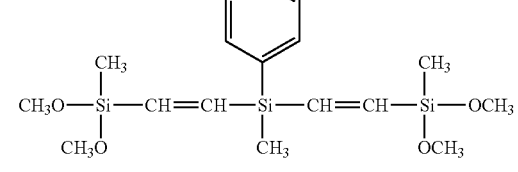

-continued

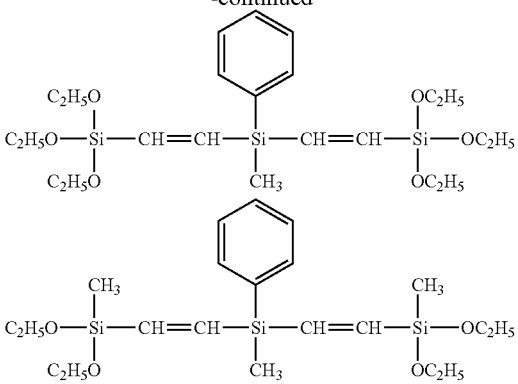

WORKING EXAMPLE

The present invention is described in detail hereunder with reference to working examples (synthesis examples), reference examples and comparative reference examples. However, the present invention is not limited to the following working examples. Further, in the specific examples below, "part" refers to "part by mass," and viscosity refers to a value measured by a rotary viscometer at 25° C.

Working Example 1

<Synthesis of Silicon-containing Compound Having Two alkoxysilyl-vinylene Groups on an Identical Silicon Atom-[bis (trimethoxysilyl-vinylene) dimethylsilane]>

Diethynyldimethylsilane of 35.0 g (0.323 mol), a 0.5 wt % toluene solution of a chloroplatinic acid ($H_2PtCl_6 \cdot 6H_2O$) of 0.10 g and toluene of 50 mL were put into a 500 mL four-necked separable flask equipped with a mechanical stirrer, a thermometer and a dropping funnel, followed by delivering thereinto 83.01 g (0.678 mol) of trimethoxysilane by drops. Later, stirring was performed at 85° C. for 6 hours, followed by performing distillation so as to obtain 106.2 g (yield 90%) of a silicon compound [bis (trimethoxysilyl-vinylene) dimethylsilane] shown below. Next, a $^1$HNMR chart of this silicon compound was analyzed, and it was confirmed that the silicon compound was the target bis (trimethoxysilyl-vinylene) dimethylsilane (trans:cis=8:1) (compound shown below). This reaction is shown in the following formula [3].

[Chemical formula 6]

[3]

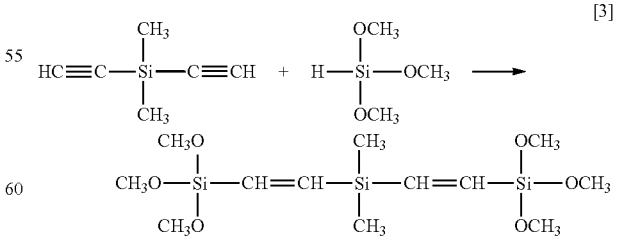

The $^1$H-NMR spectrum data of this compound are as follows.

$^1$H-NMR (400 MHz, $C_6D_6$, δ (ppm)):0.00 (s, 6H), 3.36 (s, 18H), 6.47 (d, 2H), 7.10 (d, 2H)

Working Example 2

<Synthesis of Silicon-containing Compound Having Two alkoxysilyl-vinylene Groups on an Identical Silicon Atom-[bis (trimethoxysilyl-vinylene) diphenyl silane]>

Diethynyldiphenylsilane of 34.9 g (0.151 mol), a 0.5 wt % toluene solution of a chloroplatinic acid ($H_2PtCl_6 \cdot 6H_2O$) of 0.10 g and toluene of 50 mL were put into a 500 mL four-necked separable flask equipped with a mechanical stirrer, a thermometer and a dropping funnel, followed by delivering thereinto 38.5 g (0.315 mol) of trimethoxysilane by drops. Later, stirring was performed at 85° C. for 6 hours, followed by performing distillation so as to obtain 56.5 g (yield 88%) of a silicon compound [bis (trimethoxysilyl-vinylene) diphenylsilane] shown below. Next, a $^1$HNMR chart of this silicon compound was analyzed, and it was confirmed that the silicon compound was the target bis (trimethoxysilyl-vinylene) diphenylsilane (trans:cis=9:1) (compound shown below). This reaction is shown in the following formula [4].

[Chemical formula 7]

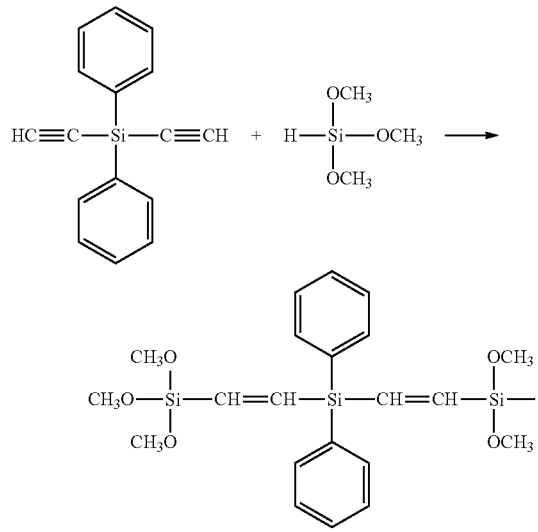

[4]

The $^1$H-NMR spectrum data of this compound are as follows.

$^1$H-NMR (400 MHz, $C_6D_6$, δ (ppm)): 3.61 (s, 18H), 6.45 (d, 2H), 7.31 (d, 2H), 7.36-7.55 (m, 10H).

Reference Example 1

Combined were 100 parts of a dimethylpolysiloxane having a viscosity of 5,000 mPa·s, and a molecular chain whose two ends are blocked by hydroxyl groups (or hydroxydimethylsiloxy groups); 4.9 parts of bis (trimethoxysilyl-vinylene) dimethylsilane; and 0.75 parts of tetramethylguanidylpropyltrimethoxysilane, followed by keeping mixing them under a moisture-blocked condition until a uniform level had been reached, thus obtaining a composition.

Reference Example 2

Combined were 100 parts of a dimethylpolysiloxane having a viscosity of 5,000 mPa·s, and a molecular chain whose two ends are blocked by hydroxyl groups (or hydroxydimethylsiloxy groups); 4.9 parts of bis (trimethoxysilyl-vinylene) dimethylsilane; and 1.0 part of an organic aluminum compound which was a mono (dipivaloylmethane) aluminum bis (ethylacetoacetate) chelate having an average structure represented by the following structural formula (2), followed by keeping mixing them under a moisture-blocked condition until a uniform level had been reached, thus obtaining a composition.

[Chemical formula 8]

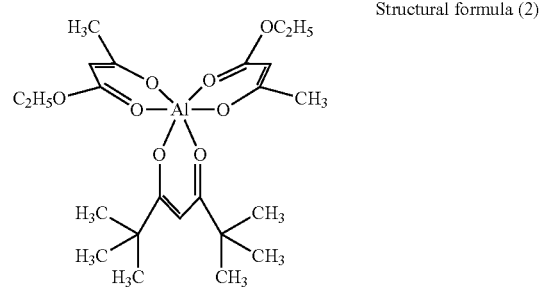

Structural formula (2)

Reference Example 3

Combined were 100 parts of a dimethylpolysiloxane having a viscosity of 5,000 mPa·s, and a molecular chain whose two ends are blocked by hydroxyl groups (or hydroxydimethylsiloxy groups); 4.9 parts of bis (trimethoxysilyl-vinylene) dimethylsilane; and 0.2 parts of a compound which was an N,N,N',N',N'',N''-hexamethyl-N'''-(trimethylsilylmethyl)-phosphorimidic triamide represented by the following structural formula (3), followed by keeping mixing them under a moisture-blocked condition until a uniform level had been reached, thus obtaining a composition.

[Chemical formula 9]

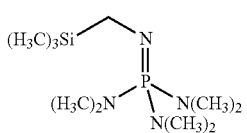

Structural formula (3)

Reference Example 4

A composition was obtained in the similar manner as reference example 1, except that 6.6 parts of bis (trimethoxysilyl vinylene) diphenylsilane was used instead of bis (trimethoxysilyl-vinylene) dimethylsilane.

Comparative Reference Examples 1 to 3

Compositions were obtained in the similar manners as reference examples 1 to 3, except that there were used 4.1 parts of a silicon compound (vinyltrimethoxysilane) represented by the following structural formula (4) instead of bis (trimethoxysilyl-vinylene) dimethylsilane.

[Chemical formula 10]

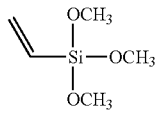

Structural formula (4)

Comparative Reference Examples 4 to 6

Compositions were obtained in the similar manners as reference examples 1 to 3, except that there were used 3.8 parts of a silicon compound (methyltrimethoxysilane) represented by the following structural formula (5) instead of bis (trimethoxysilyl-vinylene) dimethylsilane.

[Chemical formula 11]

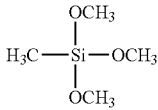

Structural formula (5)

Comparative Reference Example 7

A composition was obtained in the similar manner as reference example 1, except that there were used 4.5 parts of a silicon compound (1,6-bis (trimethoxysilyl) hexane) represented by the following structural formula (6) instead of bis (trimethoxysilyl-vinylene) dimethylsilane.

[Chemical formula 12]

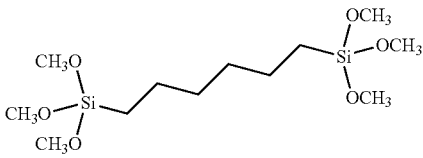

Structural formula (6)

[Measurement of Tack-free Time]

There was measured a tack-free time of each of the compositions obtained in reference examples 1 to 4; and comparative reference examples 1 to 7.

In addition, each of the compositions obtained in reference examples 1 to 4; and comparative reference examples 1 to 7 was pushed out into a sheet-like shape of a thickness of 2 mm, immediately after they had been produced. The sheet-shaped composition was then exposed to an air of 23±2° C., 50±5% RH, and left under the same atmosphere for three days so as to obtain a cured product whose properties (initial properties) were then measured in accordance with JIS K-6249. Here, a hardness was measured by a hardness meter which was an A-type durometer described in JIS K-6249.

Further, similar measurements were performed on a product obtained by storing the above cured product in a thermohygrostat of 85° C., 85% RH for 7 days. Furthermore, similar measurements were also performed on a product obtained by heating the above cured product in an oven of 150° C. for 10 days.

Table 1 shows the results of reference examples 1 and 4; and comparative reference examples 1, 4 and 7. Table 2 shows the results of reference example 2; and comparative reference examples 2 and 5. Table 3 shows the results of reference example 3; and comparative reference examples 3 and 6.

TABLE 1

| Measurement result | | Reference Example 1 | Reference Example 4 | Comparative Reference Example 1 | Comparative Reference Example 4 | Comparative Reference Example 7 |
| --- | --- | --- | --- | --- | --- | --- |
| Tack-free time (min) | | 5 | 3 | 60< | 60< | 60< |
| Initial RTV 7 days | Hardness (Durometer A) | 22 | 25 | 16 | 6 | 24 |
| | Elongation (%) | 105 | 130 | 110 | 235 | 0.33 |
| | Tensile strength (MPa) | 0.45 | 0.52 | 0.27 | 0.19 | 100 |
| Moisture resistance 85° C./85% RH 7 days | Hardness (Durometer A) | 10 | 16 | 4 | 1 | 8 |
| | Elongation (%) | 155 | 165 | 430 | 365 | 120 |
| | Tensile strength (MPa) | 0.25 | 0.27 | 0.22 | 0.08 | 0.15 |
| Heat resistance 150° C. 10 days | Hardness (Durometer A) | 20 | 20 | 15 | 12 | 23 |
| | Elongation (%) | 140 | 130 | 105 | 100 | 120 |
| | Tensile strength (MPa) | 0.47 | 0.35 | 0.23 | 0.22 | 0.29 |

TABLE 2

| Measurement result | | Reference Example 2 | Comparative Reference Example 2 | Comparative Reference Example 5 |
|---|---|---|---|---|
| Tack-free time (min) | | 2 | 10 | 15< |
| Initial RTV 7 days | Hardness (Durometer A) | 12 | 4 | 0 |
| | Elongation (%) | 105 | 210 | 430 |
| | Tensile strength (MPa) | 0.27 | 0.15 | 0.13 |
| Moisture resistance 85° C./85% RH 7 days | Hardness (Durometer A) | 11 | 0.5 | 0 |
| | Elongation (%) | 150 | 375 | 530 |
| | Tensile strength (MPa) | 0.33 | 0.16 | 0.13 |
| Heat resistance 150° C. 10 days | Hardness (Durometer A) | 18 | 15 | 14 |
| | Elongation (%) | 125 | 190 | 215 |
| | Tensile strength (MPa) | 0.45 | 0.38 | 0.38 |

TABLE 3

| Measurement result | | Reference Example 3 | Comparative Reference Example 3 | Comparative Reference Example 6 |
|---|---|---|---|---|
| Tack-free time (min) | | 4 | 60< | 60< |
| Initial RTV 7 days | Hardness (Durometer A) | 25 | 16 | 8 |
| | Elongation (%) | 100 | 105 | 215 |
| | Tensile strength (MPa) | 0.46 | 0.29 | 0.22 |
| Moisture resistance 85° C./85% RH 7 days | Hardness (Durometer A) | 15 | 10 | 6 |
| | Elongation (%) | 135 | 165 | 260 |
| | Tensile strength (MPa) | 0.33 | 0.26 | 0.25 |
| Heat resistance 150° C. 10 days | Hardness (Durometer A) | 26 | 18 | 10 |
| | Elongation (%) | 115 | 135 | 100 |
| | Tensile strength (MPa) | 0.51 | 0.31 | 0.16 |

As described above, the organic silicon compound of the present invention provides a cured product superior in fast curability and durability, and can thus serve as a curing agent component effective for a room temperature-curable organopolysiloxane composition.

However, the present invention is not limited to the above embodiment. The above embodiment is simply an example; and any embodiment belongs to the technical scope of the present invention, if the embodiment has a composition substantially identical to that of the technical ideas described in the claims of the invention, and brings about the similar function effects.

The invention claimed is:

1. A method for producing a cured product of a room temperature-curable organopolysiloxane composition, said method comprising curing said composition with an organic silicon compound represented by formula (1):

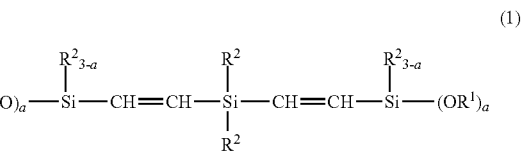

wherein $R^1$ represents either an alkyl group that has 1 to 20 carbon atoms and may have a substituted group or a cycloalkyl group that has 3 to 20 carbon atoms and may have a substituted group; $R^2$ represents either a hydrogen atom or a monovalent hydrocarbon group that has 1 to 20 carbon atoms and may have a substituted group, and each $R^2$ may be either identical or different; and each a independently represents an integer of 1 to 3.

* * * * *